(12) United States Patent
Thomas

(10) Patent No.: US 9,453,823 B2
(45) Date of Patent: Sep. 27, 2016

(54) APPARATUS FOR AND A METHOD OF IMPROVED TIMING CONTROL FOR NON-DESTRUCTIVE TESTING AND INSPECTION

(71) Applicant: Olympus NDT, Waltham, MA (US)

(72) Inventor: Andrew Thomas, Westford, MA (US)

(73) Assignee: OLYMPUS NDT, Waltham, MA (US)

( * ) Notice: Subject to any disclaimer, the term of this patent is extended or adjusted under 35 U.S.C. 154(b) by 0 days.

(21) Appl. No.: 14/449,306

(22) Filed: Aug. 1, 2014

(65) Prior Publication Data

US 2014/0338454 A1 Nov. 20, 2014

Related U.S. Application Data

(63) Continuation of application No. 13/434,276, filed on Mar. 29, 2012, now Pat. No. 8,829,763.

(51) Int. Cl.
| | |
|---|---|
| *H01L 41/04* | (2006.01) |
| *G01N 29/34* | (2006.01) |
| *G01N 29/04* | (2006.01) |
| *G01N 33/00* | (2006.01) |
| *H03K 5/13* | (2014.01) |

(52) U.S. Cl.
CPC ............ *G01N 29/343* (2013.01); *G01N 29/04* (2013.01); *G01N 29/043* (2013.01); *G01N 29/34* (2013.01); *G01N 33/00* (2013.01); *H01L 41/042* (2013.01); *G01N 2033/0096* (2013.01); *G01N 2291/0237* (2013.01); *G01N 2291/02854* (2013.01); *H03K 5/131* (2013.01)

(58) Field of Classification Search
CPC ...... G01D 5/245; G01D 5/244; G01N 29/34; G01N 29/341; G01N 29/243
USPC ............................. 310/317; 73/632; 327/170
See application file for complete search history.

(56) References Cited

U.S. PATENT DOCUMENTS 8,829,763 B2 * 9/2014 Thomas ................. G01N 29/34
310/317
2004/0256952 A1 12/2004 Ouskas

OTHER PUBLICATIONS

Office Action issued by USPO in connection with corresponding parent U.S. Appl. No. 13/434,276.

* cited by examiner

*Primary Examiner* — Derek Rosenau
(74) *Attorney, Agent, or Firm* — Ostrolenk Faber LLP

(57) ABSTRACT

A pulse generation circuit and method includes using digital signals to trigger a first and second varying analog signals and detecting when they reach one or more reference levels. In response to the first and second varying analog signals reaching one or more reference levels, a first and a second digital control signals are produced and provided as input to a pulser producing a voltage excitation pulse having a width and timing defined by the first and second digital control signals.

7 Claims, 4 Drawing Sheets

APPARATUS FOR AND A METHOD OF IMPROVED TIMING CONTROL FOR NON-DESTRUCTIVE TESTING AND INSPECTION

CROSS-REFERENCE TO RELATED APPLICATIONS

The present application is a continuation under 37 C.F.R. §1.53(b) of prior application Ser. No. 13/434,276, filed Mar. 29, 2012, by Andrew THOMAS entitled AN APPARATUS FOR AND A METHOD OF IMPROVED TIMING CONTROL FOR NON-DESTRUCTIVE TESTING AND INSPECTION, the entire contents of which are incorporated herein by reference.

FIELD OF THE INVENTION

This invention relates to non-destructive testing and inspection (NDT/NDI) particularly to high frequency NDT/NDT instruments with increased digital sampling.

BACKGROUND OF THE INVENTION

Ultrasonic thickness measurement and flaw detection devices that use ultrasonic transducers include a pulser circuit producing a high voltage excitation pulse delivered to the transducer, which in response produces an ultrasonic tuned frequency pulse designed to travel through the test piece under inspection. The ultrasonic pulse that travels into the test piece will produce ultrasonic reflections from flaws, voids or back-wall within the test piece called the return echos. Measuring the return echos allows a microprocessor based subsystem to calculate the thickness of the test piece or flaw depth within the test piece. Low frequency transducers are used for thicker test pieces and higher frequency transducers are used for thinner test pieces.

The generation of a high voltage excitation pulse is typically done with a high voltage power supply and a clocked counter to set the instance of time when the excitation pulse is generated and width of the excitation pulse. Based on the counter clock frequency and count value, this will allow the excitation pulse generation to be delayed at specific time intervals allowing it to be phase shifted as desired. By incrementally phase shifting the excitation pulse then digitally sampling each incremental phase shifted return echo, this will allow for a higher effective sampling rate of the return echo using a standard interleaving method. The time interval for phase shifting the excitation pulse has to be finer than the time interval for digitally sampling the return echo for interleaving to work in this manner.

There are other methods of interleaving and increasing the sampling rate that have inherent problems, such as using phase lock loops or delay components to fine delay the sample clock signal to the digital sampler. By incrementally delaying the clock to the digital sampler and re-sampling the return echo that appears at the same instance of time will create a higher effective sample rate but the use of phase lock loops can induce higher noise levels and clock jitter causing delay errors thus causing digital sampling rate errors. A delay component can also add higher noise and have significant delay variant from one circuit to the other.

SUMMARY OF THE INVENTION

Higher frequency ultrasonic transducers such as 125 MHz are becoming widely used due to the fact that they can inspect a very thin test piece. For a thin test piece, the time of flight which measures from the time when the excitation pulse is generated to when the return echo is received is very small; therefore a higher frequency transducer is needed to achieve these thin measurements.

In order to digitally sample a high frequency return pulse such as 125 MHz, a highly effective sample rate is needed to support the Nyquist Frequency theorem which states that a 125 MHz return echo must be digitally sampled at least twice the frequency at a rate of 250 MHz or greater. Modern day digital sampling analog to digital converters (ADC) can achieve greater than 250 MHz sampling rates but the cost and power consumption are higher and can be avoided by using a lower frequency digital sampling ADC along with interleaving as discussed in this invention.

For this invention, the generation and delay of a high voltage excitation pulse is first created by a digital counter to set the coarse delay and width which is then sent to a fine delay analog circuit such as a resistor-capacitor (RC) time constant for fine tuning the coarse delay. The digital counter for the coarse delay will create the desired excitation pulse start and width dependent on a counter clock frequency and a count value. The fine delay analog circuit will be used to finely adjust the excitation pulse delivered from the coarse delay digital counter using an RC time constant, digital to analog converter (DAC) and comparator circuit. The fine delay analog circuit will allow for finer delay adjustments of the excitation pulse then the coarse delay set by the clock frequency to the digital counter. Fine delay adjustment of the excitation pulse will in turn fine delay the return echo; therefore digitally sampling a high frequency transducer return echo can be achieved through an interleaving process.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
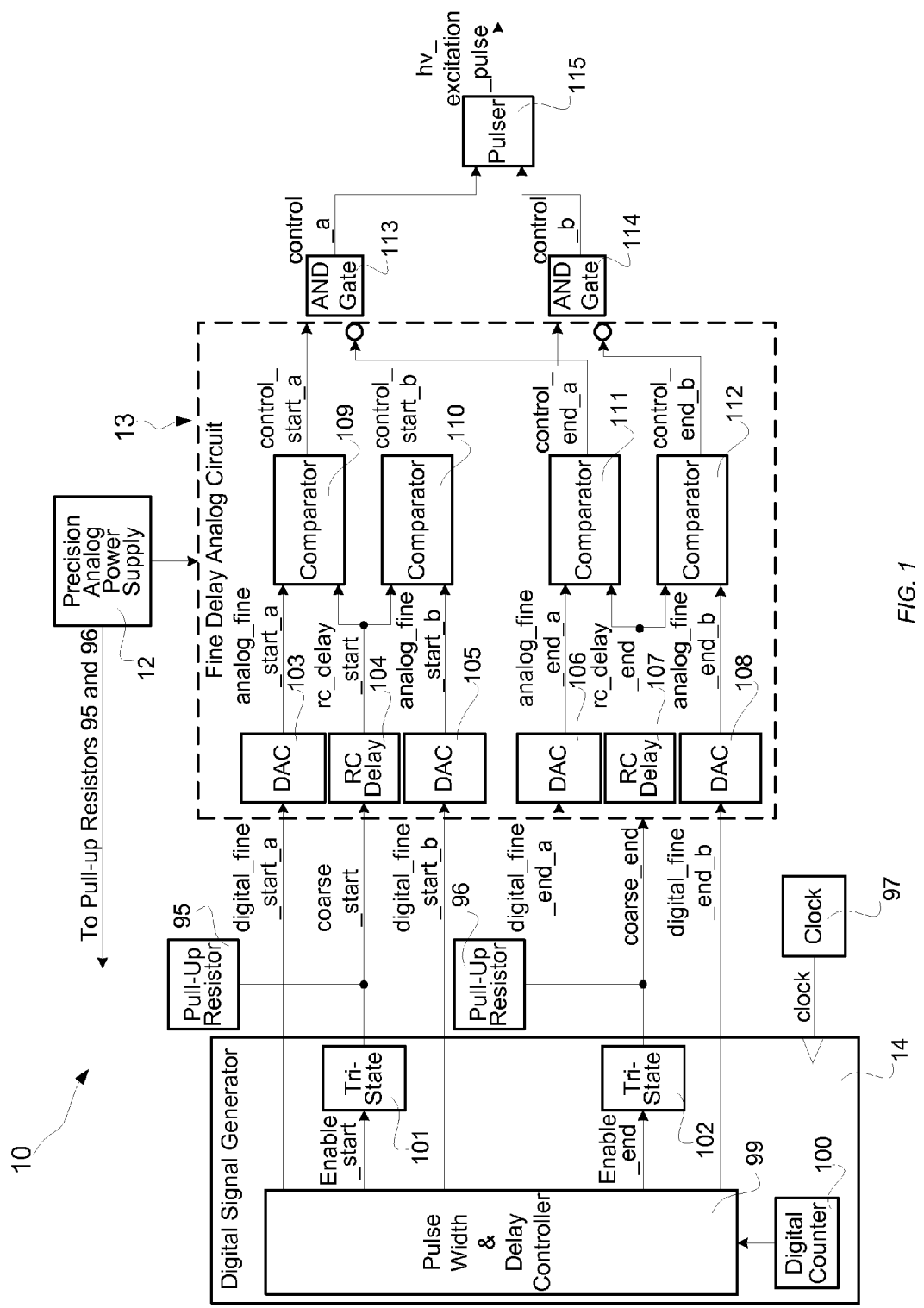
FIG. 1 is a schematic diagram showing the primary components associated with one example of a high voltage excitation pulse generator in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 depicts but one version of a circuitry 10 for generating a high voltage excitation pulse at the output of a pulser 115 which typically drives the transducer of an ultrasonic thickness measurement or flaw detection device. This high voltage excitation pulse can be hundreds of volts and have a pulse width of less than 4 ns for high frequency applications such as those involving a 125 MHz transducer. Or, conversely, the high voltage excitation pulse width can be wider for low frequency applications. And, the high voltage excitation pulse can be delayed at desired intervals for interleaving the return echo to produce higher effective sampling rates.

Referring to FIG. 1, a Digital Signal Generator 14 is the digital section of this invention and can be implemented in an FPGA, CPLD or other discrete digital components which digitally controls the coarse delay, fine delay and width of the excitation pulse through a Digital Counter 100, Pulse Width and a Delay Controller 99 and Tri-State Circuits 101, 102. Digital Counter 100 has its count rate set by an input Clock 97 which can be an oscillator or other digital clock generator that sets the resolution of the coarse delay and width for the excitation pulse.

Continuing with FIG. 1, Digital Counter 100 is compared to a desired start count value in Pulse Width and Delay Controller 99 to dictate when the coarse start of the excitation pulse begins by asserting the enable_start signal to Tri-State Circuit 101. The Digital Counter 100 is also compared to a desired end count value in the Pulse Width and Delay Controller 99 to dictate the coarse end of the excitation pulse by asserting the enable_end signal to the Tri-State Circuit 102.

Tri-State circuits 101 and 102 are digital tri-state buffers in which their respective output is driven to 0 or a high impedance state to RC Delay components 104 and 107, respectively with Pull-Up Resistor 95 on signal coarse_start and Pull-Up Resistor 96 on signal coarse_end. When signals enable_start and enable_end from Pulse Width and Delay Controller 99 are not enabled, this will drive the Tri-State Circuits 101, 102 to a high impedance state and the outputs coarse_start and coarse_end are pulled high through Pull-Up Resistors 95 and 96. On the other hand, when signals enable_start and enable_end are enabled, this drives the output coarse_start and coarse_end to 0 to set the coarse width and delay of the excitation pulse. The coarse_start and coarse_end falling edges can be several clock cycles apart depicted in FIG. 2 or generated on the same clock edge as depicted in FIG. 3 to produce a narrower excitation pulse resolution than the clock value allows. The narrow excitation pulse width is required for high frequency transducers such as 125 MHz.

Reference is still made to FIG. 1. Tri-state circuits 101 and 102 allow for decoupling of the digital power supply to a low noise Precision Analog Power Supply 12 through the pull-up resistors 95 and 96 on coarse_start and coarse_end signals thus eliminating the digital power supplies which may be noisy. The low noise Precision Analog Power Supply 12 can be one of a precision voltage reference device which feeds all the remaining Fine Delay Analog Circuits 13 including pull-ups 95 and 96 on coarse_start and coarse end. A common low noise Precision Analog Power Supply 12 allows for more precise delay for finer adjustment through the analog circuits.

Figure 2:
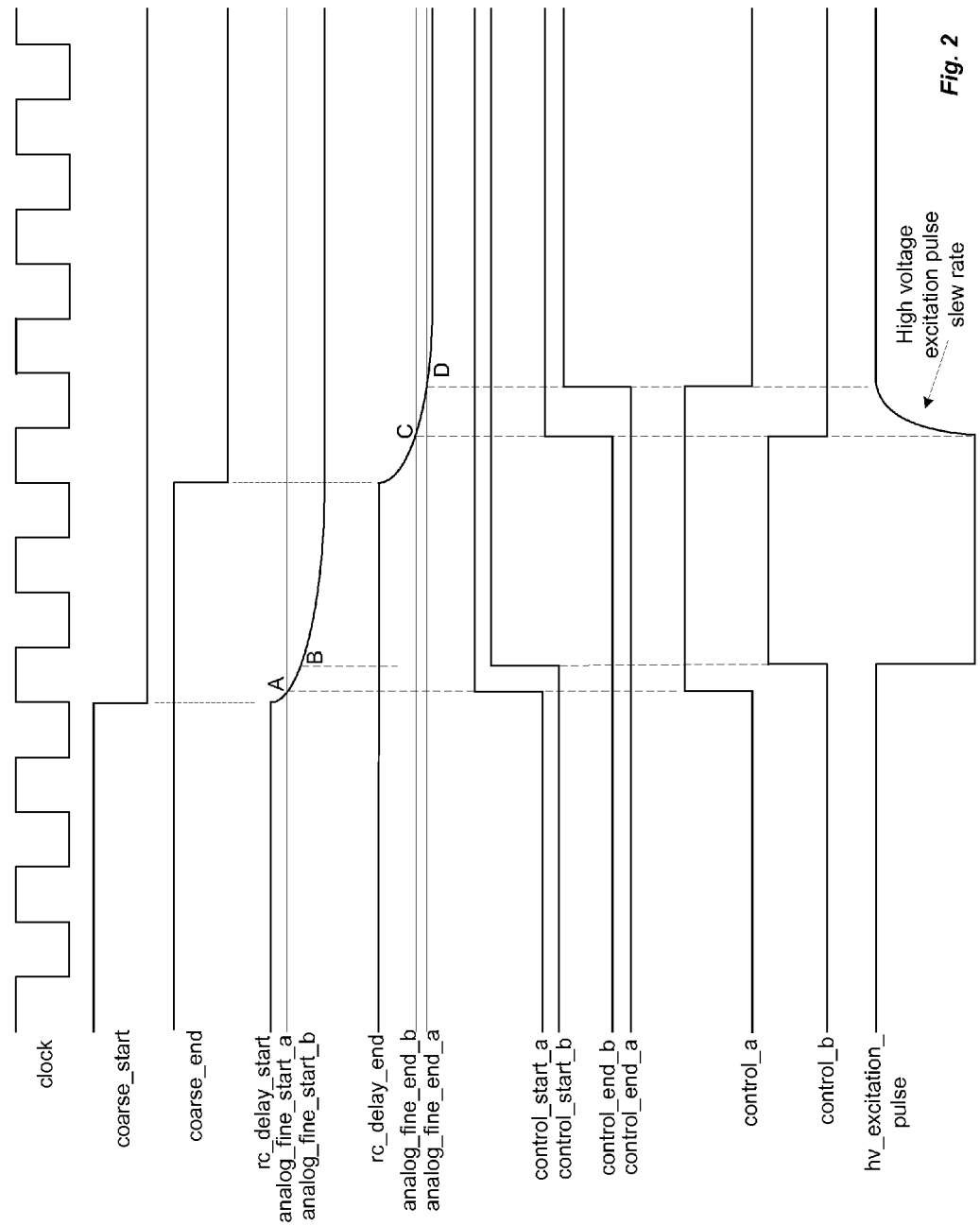
FIG. 2 is timing diagram showing the signals produced by the various components shown in FIG. 1 resulting in a fairly low frequency excitation voltage pulse.
Figure 3:
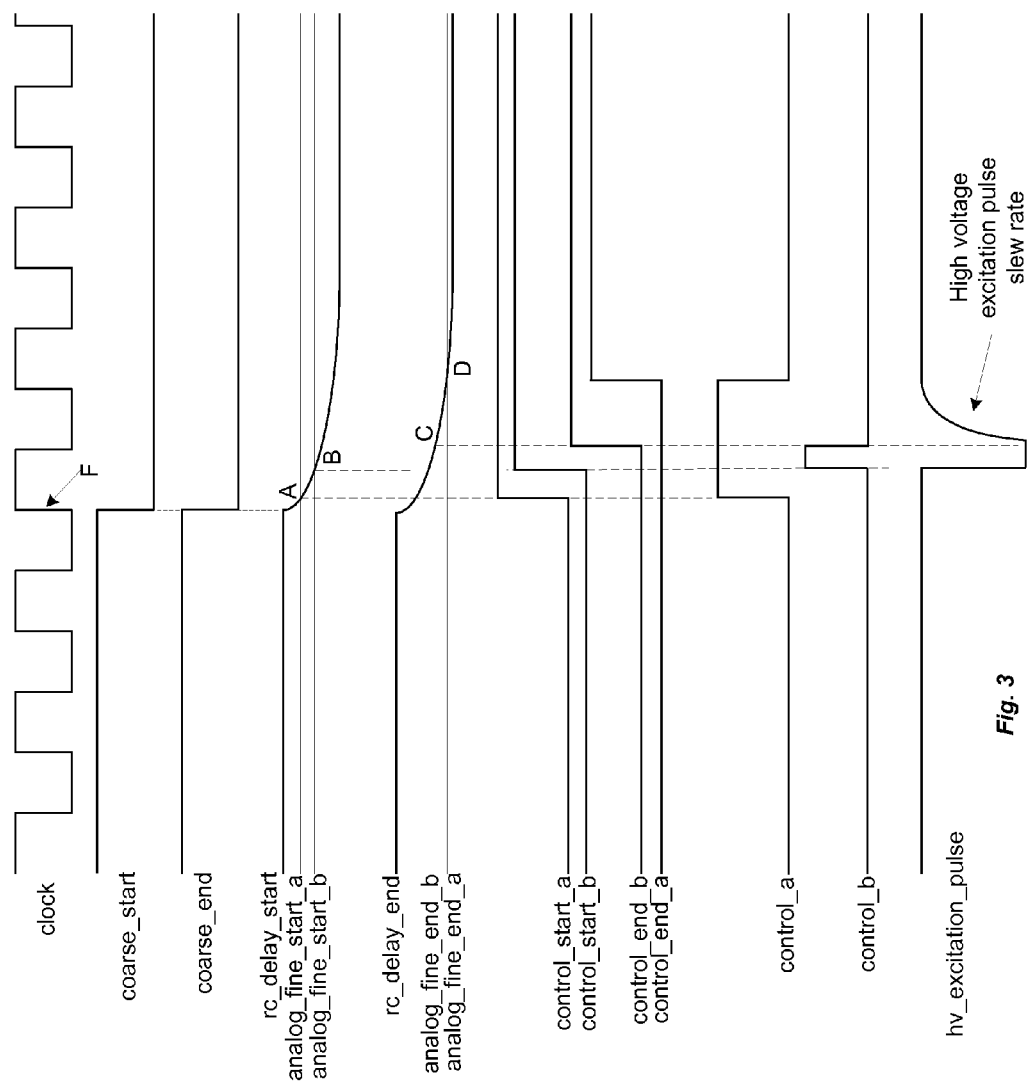
FIG. 3 is a timing diagram showing the capability of excitation pulse generator of FIG. 1 producing a high frequency excitation voltage pulse narrower than one clock pulse for a 125 MHz transducer.

Reference is now made primarily to FIG. 1, assisted by referring to FIGS. 2 and 3. The digital values digital_fine_start_a and digital_fine_start_b from Pulse Width and Delay Controller 99 are converted to an analog voltage reference called analog_fine_start_a and analog_fine_start_b by a digital to analog converter (DAC) 103 and 105 which are used set the fine delay start A and fine delay start B of the excitation pulse (shown in FIGS. 2 and 3). The digital values digital_fine_end_a and digital_fine_end_b from Pulse Width and Delay Controller 99 are converted to an analog voltage reference called analog_fine_end_a and analog_fine_end_b through a digital to analog converter (DAC) 106 and 108 and which are used to set the fine delay end points of the excitation pulse (shown as C and D, respectively in FIGS. 2 and 3).

FIGS. 1, 2 and 3, RC delays or RC delay components 104 and 107 are analog circuits which have a discrete resistor and capacitor to create an exponentially decaying voltage as shown in FIGS. 2 and 3, with signals named as rc_delay_start and rc_delay_end created from the input signals coarse_start and coarse_end as shown in FIG. 2 and FIG. 3. The exponential decay rate is based on the selection of the resistor and capacitor, which is known to those skilled in the art. In one example, a 1K ohm resistor and 22 pf capacitor were used. The RC circuit should preferably have low impedance with low resistance and high capacitor values. The reason is because a resistor with high resistance may have a high stray capacitance and can generate a large RC time constant error. With an extremely large RC time constant, the noise in the RC circuit may cause output errors to the comparator and make the excitation pulse timing and width unpredictable. The preferred time constant will be approximately two digital clock cycles.

Still referring to FIGS. 1, 2 and 3, the exponentially decaying voltage rc_delay_start from RC Delay 104 is compared to voltage references analog_fine_start_a and analog_fine_start_b through comparator 109 and 110. When rc_delay_start is equal to or less than the voltage references analog_fine_start_a and analog_fine_start_b, control_start_a and control_start_b will go high respectively to set the fine delay start points of the excitation pulse as depicted as A and B respectively in FIGS. 2 and 3.

Similarly, the exponentially decaying voltage rc_delay_end from RC Delay 107 will be compared to voltage references analog_fine_end_a and analog_fine_end_b through comparator 111 and 112. When rc_delay_end is equal to or less than the voltage references analog_fine_end_a and analog_fine_end_b, control_end_a and control_end_b will go high respectively to set the fine delay end points of the excitation pulse as C and D depicted in FIG. 2 and FIG. 3. The fine delay and width of the excitation pulse is set based on the desired settings of DAC 103, 105, 106 and 108.

Referring to FIG. 1, comparators 109 and 111 output signals control_start_a and control_end_a which are fed to AND Gate 113 to produce control_a to set the start and end of upper control to the high voltage Pulser 115, as seen in hv_excitation_pulse in FIGS. 2 and 3. When signal control_start_a, a non-Inverting input to the AND Gate 113 and signal control_end_a, an inverting nput to the AND Gate 113 are both low, then control_a will be low. When control_start_a goes high and control_end_a goes low then control_a goes high, when control_start_a stays high and control_end_a goes high then control_a goes low as depicted in FIG. 2 and FIG. 3.

Similarly, comparators 110 and 112 provide output signals control_start_b and control_end_b go to AND gate 114 to produce control_b to set the start and end of lower control to the high voltage Pulser 115. When signal control_start_b (Non Inverting Input to the AND Gate 114) and signal control_end_b (Inverting Input to the AND Gate 114) are both low then control_b will be low. When control_start_b goes high and control_end_b goes low then control_b goes high, when control_start_b stays high and control_end_b goes high then control_b goes low as depicted in FIG. 2 and FIG. 3.

Figure 4:
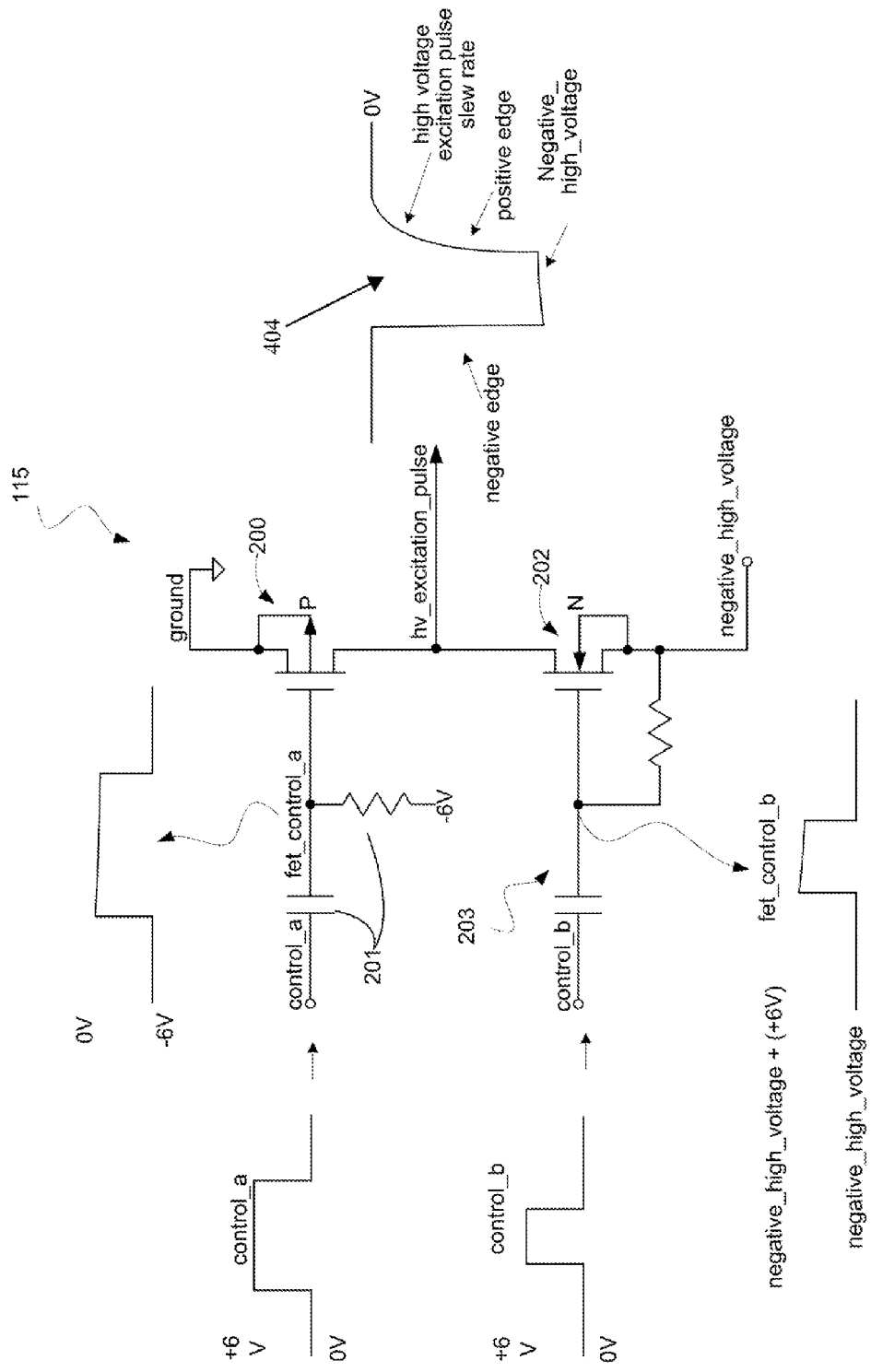
FIG. 4 is a schematic circuit diagram depicting an example of the circuitry of pulser 115 of FIG. 1.

Reference is now primarily made to FIG. 2, assisted by referring back to FIG. 1. FIG. 2 shows the timing diagram depicting an example of an excitation pulse width targeted to be greater than a single digital clock cycle. The signal clock is the digital clock which feeds the Digital Signal Generator to produce the coarse_start and coarse_end signals. The coarse_start and coarse_end signals provided by tri-state circuit 101 and 102, respectively, feed the RC Delays 104 and 107 to produce the decaying voltage signals rc_delay_start and rc_delay_end respectively, based on the resistor and capacitor selection. The decaying voltage signal rc_delay_start is compared to a reference voltage signals analog_fine_start_a and analog_fine_start_b by comparators 109 and 110, respectively. When rc_delay_start is equal to or less than reference voltage signals analog_fine_start_a and analog_fine_start_b, control_start_a and control_start_b goes high respectively to set fine delay start A and fine delay start B, respectively, in the excitation pulse. The decaying voltage signal rc_delay_end is compared to a reference voltage analog_fine_end_a and analog_fine_end_b by comparators 111 and 112. When rc_delay_end is equal to or less than reference voltage signals analog_fine_end_a and analog_fine_end_b, control_end_a and control_end_b goes high respectively to set fine delay end points C and D of the excitation pulse. The signals control_start_a and control_end_a go through AND Gate 113 to produce control_a to control the upper FET 200 of the excitation pulse. The signals control_start_b and control_end_b go through AND Gate 114 to produce control_b to control the lower FET 202 of the excitation pulse. (FET signals are shown in FIG. 4). Pulser 115 generates the signal hv_excitation_pulse to the ultrasonic transducer in response to control signals control_a and control_b from AND Gates 113 and 114, respectively.

Reference is now primarily made to FIG. 3, assisted by referring back to FIG. 1. As seen in FIG. 3, for higher frequency applications such as with 125 MHz, it is desirable that the excitation pulse width be 4 ns or less which may be a smaller time interval than the clock to the Digital Signal Generator can provide. In order to create a narrower pulse width than the clock signal allows, the coarse_start and coarse_end values need to drop low at the same instance of the clock cycle and the remaining delay will be controlled through fine delay only. The signal clock 100 is the digital clock which feeds the Digital Signal Generator 99 to set the coarse_start and coarse_end at the same time. The signal coarse_start and coarse_end feed the RC Delays 104 and 107 to produce the decaying voltage rc_delay_start and rc_delay_end signals, respectively based on the resistor and capacitor selection. The decaying voltage signal rc_delay_start is compared to a reference voltage signals analog_fine_start_a and analog_fine_start_b by comparators 109 and 110. When rc_delay_start is equal to or less than reference voltage signals analog_fine_start_a and analog_fine_start_b, control_start_a and control_start_b increase respectively to set fine delay start A and fine delay state B of the excitation pulse. The decaying voltage rc_delay_end is compared to reference voltage analog_fine_end_a and analog_fine_end_b by comparators 111 and 112, respectively. When rc_delay_start is equal to or less than reference voltage signals analog_fine_start_a and analog_fine_start_b, control_end_a and control_end_b increase respectively to set fine delay end points of C and D of excitation pulse. The signals control_start_a and control_end_a will go through an AND Gate to produce control_a to control the upper FET 200 of the excitation pulse. The signals control_start_b and control_end_b go through AND Gate 114 to produce control_b to control the lower FET 202 of the excitation pulse. Pulser control circuit 115 then generates the signal hv_excitation_pulse to the ultrasonic transducer in response to control signals control_a and control_b from AND Gates 113 and 114.

Reference now is made to FIG. 4, assisted with referring back to FIG. 1. As it is explain above that pulser 115 generates the high voltage excitation pulse to the ultrasonic transducer (not shown) in response to control signals control_a and control_b from AND Gates 113 and 114. The control_a signal from AND gate 113 controls the gate of a field effect transistor (FET) to control the ground of pulser 115. The control_b signal from AND gate 114 controls the gate of a field effect transistor (FET) to control the high voltage of pulser 115 which is typically a negative voltage.

Continuing with FIG. 4, a more elaborated circuit design for pulser 115 is shown with the upper P-channel FET 200 controlling ground and lower N-channel FET 202 controlling the negative_high_voltage (e.g., −200 volts) through signals control_a and control_b, respectively. Signal comes in on control_b and produces signal fet_control_b through an RC circuit 203 to control the negative edge (alternatively called falling or leading edge) of the hv_excitation_pulse output signal 404. Signal comes in on control_a and produces signal fet_control_a through an RC circuit 201 to control the positive edge (alternatively called rising edge or trailing edge) of the hv_excitation_pulse output signal 404. Since the signals control_a and control_b are positive voltages and negative voltages are needed to drive the P-channel FET 200 and N-channel FET 202 then capacitors are needed as shown in RC circuits 201 and 203. Signal fed as control_a and signal fed as control_b to RC circuits 201 and 203, respectively, are offset in time to avoid shoot-through current through the FET's. The gap between the trailing edge of signal control_a and signal control_b determines the slew rate of the high voltage excitation pulse as shown in output signal hv_excitation_pulse. It is important to note that keeping the gap in an optimal range as an advantage of the subject circuitry since the fine delay analog circuit can control the rising and falling edges of the control signal precisely. When the gap is too small, the risk of shoot-through current increases; when the gap is too large, the excitation pulse may not behave as desired. It is known to those skilled in the art to produce the hv_excitation_pulse output signal feeding to an ultrasonic transducer (not shown).

It is important to note and to be appreciated by those skilled in the art that the nature of negative or positive voltage of the control signals and the excitation pulse are for exemplary purposes. The framework of the timing control method herein disclosed applying to a signal with negative voltage would equally apply to a similar signal with positive voltage.

Referring back to FIG. 1, an important aspect of the present disclosure should be noted is that Digital Signal Generator 14 can be configured to produce a wide variety of desirable and stable excitation pulses and the downstream circuitry does not change. By employing circuitry as shown in FIG. 1 (or circuitry equivalent thereto) where both digital and analog signals work together to achieve a desirable range of excitation pulse widths and delay allows the invention to achieve fine continuous control of the excitation pulse and achieve a fractional clock period pulse width in contrast to conventional digital pulse generation methods.

In one example to generate an excitation pulse width of 13.75 ns with a digital clock frequency of 200 MHZ (5 ns) to the Digital Signal Generator 14, the coarse_start and coarse_end width between these signals are set by the integer quotient (13.75 ns/5 ns=2.75) 2 to set the coarse width of 10 ns. The remaining (5 ns*0.75) 3.75 ns delay will be done through the analog fine delay circuits by delaying the fine delay end only to achieve an overall excitation pulse width of 13.75 ns.

Having coarse and fine delay capabilities of the high voltage excitation pulse to the ultrasonic transducer allows the return echos to be delayed accordingly. Therefore the process of interleaving can be accomplished by incrementally delaying the high voltage excitation pulse and digitally sampling the delayed return echos through an analog to digital converter (ADC). This method of interleaving increases the digital sampling rate of the return echoes.

It should be noted that some terms can be alternatively used in the present disclosure as follow.

analog_fine_start_a can be alternatively used as a first reference signal;
analog_fine_end_a can be alternatively used as a second reference signal;
analog_fine_start_b can be alternatively used as a third reference signal;
analog_fine_end_b can be alternatively used as a first reference signal.

It should further be noted that some terms can be alternatively used in the present disclosure as follow.

Comparator 109 can be alternatively used as a first reference signal;
Comparator 111 can be alternatively used as a second reference signal;
comparator 110 can be alternatively used as a third reference signal;
comparator 112 can be alternatively used as a first reference signal.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. For example, the analog delay circuitry may include devices or components different than the RC circuits discussed herein.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A pulse generation method comprising:
    producing a coarse start digital signal, and a coarse end digital signal, by using a digital signal generator;
    producing a first varying analog signal by using a first delay circuit;
    producing a second varying analog signal by using a second delay circuit;
    producing a first digital control pulse in response to the first varying analog signal and a first reference signal and in response to the second varying analog signal and a second reference signal by using a first control pulse generator circuit;
    producing a second digital control signal pulse from the first varying analog signal and a third reference signal and from the second varying analog signal and a fourth reference signal by using a second control pulse generator circuit; and
    generating a pulse having a leading edge controlled by a said digital control pulse and a width controlled by the first and second digital control pulses by using a pulser circuit.

2. The method of claim 1 in which the leading edge of the pulse is controlled by the leading edge of the second digital control pulse and the width of the pulse is controlled by the gap between the trailing edges of the first and second digital control pulses.

3. The method of claim 1 in which the coarse start digital signal and coarse end digital signal are generated in response to a clock signal, producing the coarse start digital signal and the coarse end digital signals, respectively.

4. The method of claim 1 in which the first varying analog signal is a first discharging voltage level.

5. The method of claim 1 in which the second varying analog signal is a second discharging voltage level.

6. The method of claim 1 in which generating a first digital control pulse includes:
    comparing the first discharge voltage level to a first reference signal to construct the leading edge of the first digital control pulse, and
    comparing the second discharging voltage level with a second reference signal to construct the trailing edge of the first digital control pulse.

7. The method of claim 1 in which producing the second digital control pulse includes:
    comparing the first discharging voltage level to a third reference signal to construct the leading edge of the second digital control pulse, and
    comparing the second discharging voltage level with a fourth reference signal to construct the trailing edge of the second digital control pulse.

\* \* \* \* \*